United States Patent
Barac et al.

(10) Patent No.: US 6,756,514 B1
(45) Date of Patent: Jun. 29, 2004

(54) INTEGRATED DIMERIZATION PROCESS

(75) Inventors: George Barac, St. Charles, IL (US); Larry L. Bendig, Houston, TX (US); William L. Cox, Houston, TX (US); Larry H. Nemec, Houston, TX (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 10/314,567

(22) Filed: Dec. 9, 2002

(51) Int. Cl.[7] .............................. C07C 2/06; C07C 2/88
(52) U.S. Cl. ...................................... 585/328; 585/329
(58) Field of Search .................................. 585/328, 324

(56) References Cited

U.S. PATENT DOCUMENTS

| | | |
|---|---|---|
| 2,695,327 A | 11/1954 | Ziegler et al. ......... 260/683.15 |
| 4,172,855 A | 10/1979 | Shubkin et al. ................ 585/16 |
| 4,973,788 A | 11/1990 | Lin et al. ..................... 585/511 |
| 5,625,105 A | 4/1997 | Lin et al. ..................... 585/511 |
| 5,663,469 A | 9/1997 | Krzystowcryk et al. .... 585/503 |

*Primary Examiner*—Thuan D Dang
(74) *Attorney, Agent, or Firm*—James R. Henes

(57) ABSTRACT

A process for dimerizing vinyl olefins that is fully integrated into a process for making vinyl olefins is disclosed.

12 Claims, 3 Drawing Sheets

INTEGRATED DIMERIZATION PROCESS

BACKGROUND OF THE INVENTION

1. Field of the Invention

The present invention relates to a process for dimerizing vinyl olefins and more particularly relates to such a dimerization process which is fully integrated into a process for manufacturing vinyl olefins.

2. Discussion of the Prior Art

Vinylidene olefins are of commercial importance as raw materials for use in producing double tailed oxo alcohols and other functionalized derivatives, used in the manufacture of detergents, surfactants, specialty agricultural chemicals, and fuel or lubricant additives. Vinylidenes may also dimerized using a Friedel Crafts catalyst to form valuable synthetic lubricants as described in Shubkin, U.S. Pat. No. 4,172,855. Vinylidenes can be produced by dimerizing vinyl olefins. As described in Ziegler, U.S. Pat. No. 2,695,327 vinyl olefins can be dimerized using an alkyl aluminum catalyst to form vinylidenes primarily and a much smaller amount of a non-vinylidene dimer referred to herein as a "deep internal dimer." Vinylolefins can also be dimerized to form "deep internal olefin dimers" primarily using a catalyst such as a Friedel Crafts catalyst (for example, $BF_3$). The present invention is not concerned with such Friedel Crafts catalyzed dimerizations.

Numerous processes for dimerizing vinyl olefins to form vinylidenes have been disclosed. Shubkin et al., U.S. Pat. No. 4,172,855 (Oct. 30, 1979), discloses alkyl aluminum compounds as preferred catalysts for such dimerization and at a useful level of 0.1 to 10 weight percent based on the weight of the vinyl olefin and over a wide temperature range of about 50°–250° C. or higher depending on the particular catalyst employed. In one example, approximately 85 percent of 1-octene at an initial weight of 400 grams was converted after reacting over a weekend at 120–130° C. in the presence of 38.5 milliliters of tri-n-butyl aluminum Lin et al., U.S. Pat. No. 4,973,788 (Nov. 27, 1990) describes a process for dimerizing a vinyl olefin monomer at a selectivity of at least 85 mole percent. This is accomplished by the use of a catalyst which consists essentially of 0.001–0.04 mole of trialkylaluminum per mole of vinyl olefin, and conducting the reaction at a temperature in the range of about 100°–140° C. for a time sufficient to convert at least 80 mole percent of the initial vinyl olefin to a different product. The reaction rate under these conditions is quite slow, and thus a long reaction time is required. For example, it is pointed out that the time required for 90 percent conversion at 120° C. with 0.043 mole of aluminum alkyl catalyst per mole of initial vinyl olefin is about 94 hours, and that with 0.017 mole of the catalyst per mole of initial vinyl olefin the time required at 120° C. is about 192 hours. It is also shown in the patent that, although the reaction is faster at 172° C. compared to 120° C., the selectivity to vinylidene dimer is only 71 percent compared to 90 percent with the same catalyst concentration but at 120° C. Similarly the selectivity of the conversion of the vinyl olefin to form vinylidene dimer decreased sharply as the catalyst concentration was increased above 0.043 (and up to 0.67) mole of catalyst per mole of initial vinyl olefin. The patent states that the use of larger amounts of aluminum alkyls result in the formation of unacceptably large quantities of internal olefins, both monomeric and dimeric.

In the presence of aluminum alkyl, vinyl olefins are dimerized to vinylidene olefins via the Markovnikov route. However, a competing reaction which adversely affects the yield of vinylidene olefin or the purity thereof is the isomerization of the vinylidene dimer to deep internal olefin dimer via the anti-Markovnikov route. Another undesirable competing reaction which normally tends to occur at dimerization temperatures is the isomerization of the vinyl olefin monomer to internal isomer olefin monomer via a aluminum hydride route or by other known mechanisms. Such internal olefin formation adversely affects the dimer selectivity.

Lin et al., U.S. Pat. No. 5,625,105 (Apr. 29, 1997) discloses that vinyl olefins can be dimerized to vinylidenes in good yield and in shorter reaction periods than those reported in the aforesaid Lin et al. U.S. Pat. No. 4,973,788 by using a trialkyl aluminum catalyst in the range of 0.001 to 0.05 mole of catalyst per mole of initial vinyl olefin at a temperature of 140° to 170° C.

Krzystowczyk et al., U.S. Pat. No. 5,663,469 (Sep. 2, 1997), discloses the formation of vinylidene olefins in good yield and high selectivity and in shorter reaction periods through the use of 0.001 to 0.5 mole of trialkyl aluminum catalyst per mole of the initial vinyl olefin, at a temperature of 100° to 200° C., provided that the reaction mixture is in direct contact with a nickel-containing metal alloy surface for at least one hour at a temperature above about 50° C. and that at least one acetylenic hydrocarbon is added to the reaction mixture prior to such contact in an amount that is at least sufficient to inhibit double bond isomerization in the reaction mixture but insufficient to inhibit formation.

Thus far, prior art methods have been directed at suppressing competing double bond isomerization leading to the formation of internal isomer monomers and of deep internal olefin dimers and at the expense of relatively long reaction times. There has been no disclosure of any attempt to further reduce the length of the dimerization reaction to two hours or less and to incorporate the dimerization into a process that would better utilize the products of the aforesaid competing reactions.

OBJECTS OF THE INVENTION

It is therefore a general object of the present invention to provide an improved process for dimerizing vinyl olefins that affords such benefits.

More particularly, it is an object of the present invention to provide an improved aforesaid process that increases the rate of conversion of vinyl olefins to vinylidenes and deep internal olefins.

It is another object of the present invention to provide an improved aforesaid process that makes efficient use of unreacted vinyl olefins and products of the aforesaid competing reactions that form deep internal olefin dimers and internal isomer olefin monomers.

It is a related object of the present invention to provide an improved aforesaid process which is incorporated into a process for making vinyl olefins.

Other objects and advantages of the present invention will become apparent upon reading the following attached description and appended claims.

SUMMARY OF THE INVENTION

The present invention is an improvement in a process for manufacturing vinyl olefins containing from 4 to 30 carbon atoms, comprising: (1) reacting ethylene in a chain growth reaction in the presence of an alkyl aluminum chain growth catalyst in at least one chain growth step (2) displacing the alkyl moieties of the resulting alkyl aluminum chain growth product to form a displacement product mixture comprising the corresponding vinyl olefins formed from the alkyl moieties in at least one displacement step; (3) fractionating the displacement product mixture from at least one aforesaid displacement step to separate a liquid fraction comprising vinyl olefins containing from 4 to 30 carbon atoms; and (4)

fractionating the resulting liquid fraction to separate therefrom a lower molecular weight fraction comprising the aforesaid vinyl olefins. The improvement comprises: (5) dimerizing vinyl olefins to form vinylidenes and deep internal olefins in the presence of a dimerization catalyst comprising alkyl aluminum at a initial molar ratio of alkyl aluminum to vinyl olefin of from about 0.01:1 to about 1.5:1 and at a temperature in the range of from 200° C. to about 288° C. for a period of time in a range of from about 30 to about 120 minutes at a selectivity for the formation of vinylidenes and deep internal olefins of at least 50 mole percent; and (6) treating the resulting dimerization product mixture by (a) combining it in its entirety with the feed to at least one aforesaid chain growth step (1) or the feed to at least one aforesaid displacement step (2); or (b) combining it in its entirety with the product mixture from at least one aforesaid chain growth step (1) or with the product mixture from at least one aforesaid displacement step (2); or (c) fractionating it to separate a light olefin fraction and a heavier fraction comprising vinylidenes and deep internal olefins which heavier fraction is then treated as in step (a) or (b); such that the resulting displacement product mixture comprises vinylidenes and deep internal olefins from the dimerization product mixture or chain growth products of such vinylidenes and deep internal olefins which are separated with the aforesaid vinyl olefins in the liquid fraction separated in step (3) and are subsequently separated as the higher molecular weight fraction from the vinyl olefins in step (4).

BRIEF DESCRIPTION OF THE DRAWINGS

For a more complete understanding of this invention, reference should now be made to the embodiments illustrated in greater detail in the accompanying drawings and described below by way of examples of the invention. In the drawings.

Figure 1:
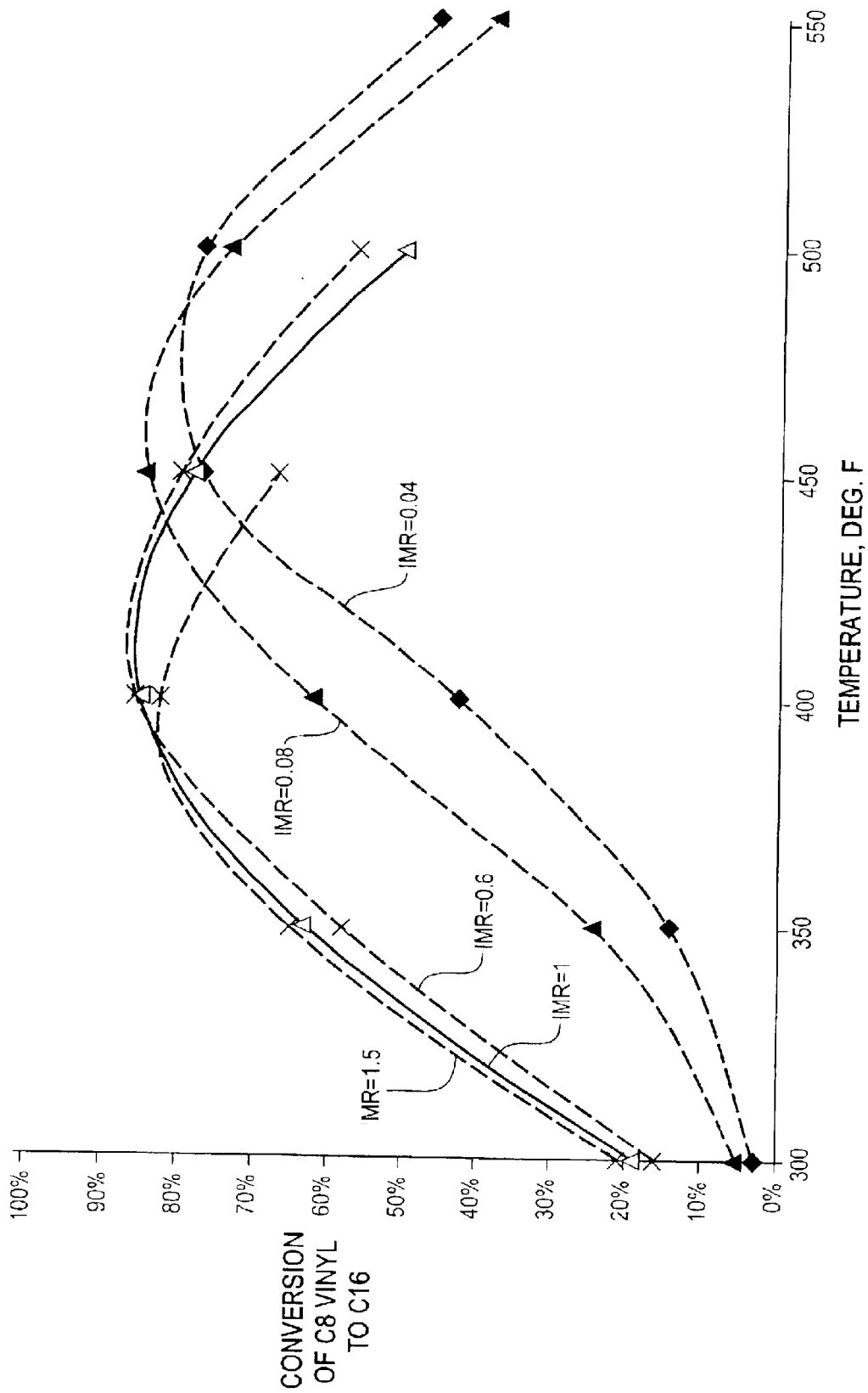
FIG. 1 is a plot of the selectivities for the formation of vinylidenes from the dimerization of vinyl olefin versus reaction temperatures at each of five different initial mole ratios of dimerization catalyst to the vinyl olefin and at a reaction time of 30 minutes derived from a computer simulation of the dimerization.

It should be understood, of course, that the invention is not necessarily limited to the particular embodiment illustrated in the drawings.

DETAILED DESCRIPTION

For the purpose of this specification; olefins are referred to as "vinyl olefins" or R—CH=CH$_2$; "vinylidene olefins" or

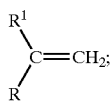

and internal olefins, which are sub-divided as: "di-substituted olefins" or R$^1$—CH=CH—R, "tri-substituted olefins" or

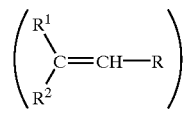

and "tetra-substituted olefins" or

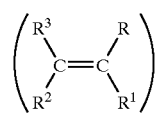

wherein R, R$^1$, R$^2$ and R$^3$ represent a hydrocarbyl group. Internal olefins are also classified as "beta-internal olefins" in which the double bond is connected to the beta-carbon atom as in:

R—CH=CH—CH$_3$ and "deep internal olefins" which are di-substituted olefins in which the double bond is further towards the center of the olefin as in:

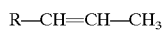

wherein R$^{1'}$ and R$^{2'}$ are different by two or four carbon numbers and are aliphatic hydrocarbon groups containing two or more carbon atoms.

The "beta-internal olefins" referred to herein are monomeric. This means they contain the same number of carbon atoms as the initial vinyl-olefins from which they are formed but the olefinic double bond has moved toward the center of the molecule, by just one carbon number (i.e., the double bond is at the second carbon number).

The "deep internal olefins" referred to herein are dimers of the initial vinyl olefins from which they are formed. For example, a deep internal dimer of 1-octene contains 16 carbon atoms. They differ from vinylidene dimers in that their olefinic double bond is in the linear chain near the center of the molecule.

The vinylidene olefins are useful when oligomerized as oils. Depending on their viscosity, different applications for such oils are known, for example, as lubricants. These materials are mixtures of different percentages of dimer, trimer, tetramer, pentamer and higher oligomers which oligomers are produced in different proportions in the oligomerization process. Due to the increasing use of dimers, both vinylidenes and the aforesaid "deep internal olefins," in applications such as low temperature lubricants and drilling fluids, methods for the preferential production of both types of dimers are of interest.

The olefins that are dimerized to make such dimers are predominately (at least 50 mole percent) C$_4$ to C$_{20}$ straight- or branched-chain monoolefinically unsaturated hydrocarbon (but not less than 5 mole percent) in which the olefinic unsaturation occurs at the 1- or alpha-position of the carbon chain. Typically they have the following formula

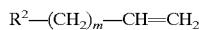

where R$^2$ is hydrogen or alkyl, that is, C$_1$ to C$_{16}$ linear or branched alkyl, preferably C$_1$ to C$_6$ linear or branched alkyl, most preferably C$_1$ to C$_4$ linear or branched alkyl, for example, methyl, ethyl and the like, and m is an integer from 0 to 18.

Linear alpha-olefins are commercially available and can be made by the welt known Ziegler ethylene chain growth and displacement on trialkyl aluminum. Individual olefins may be used as well as mixtures of such olefins. Examples of suitable olefins are 1-hexene, 1-heptene, 1-octene, 1-nonene, 1-ecene, 1-dodecene, 1-hexadecene and 1-tetradecene. The more preferred normal alpha-olefin monomers are those containing about 6–18 carbon atoms.

Typically the vinyl olefins used in the process will contain in the range of about 3 to about 30 or more carbon atoms per molecule. The initial vinyl olefin will contain preferably in the range of 4 to 20, and more preferably in the range of 6 to 18 carbon atoms per molecule. For some end use applications, it is desirable to use a substantially pure single vinyl olefin, such as 1-butene, 1-pentene, 1-hexene, 1-octene, 1-decene, or 1-tetradecene. For other end use applications mixtures of vinyl olefins are entirely suitable. In such case co-dimerization takes place.

Any straight chain or branched chain trialkylaluminum compound can used as the catalytic component charged to the dimerization reaction zone in the practice of this invention. However, it is a critical future of the method of this invention that a trialkyaluminum catalyst is employed for both the chain growth and dimerization steps. Typically the alkyl groups will contain from 1 to 30 carbon atoms, and preferably in the range of 2 to about 18 carbon atoms each. Most preferred as trialkyaluminum compounds such as triethylaluminum tri-isobutyl aluminum, tributylaluminum, trihexylaluminum, trioctylaluminum, tris(decyl)aluminum, tris(tetradecyl) aluminum, and the like. Mixtures of aluminum trialkyls can be also used if desired. The hydride content, if any, of the aluminum trialkyl should be quite low, for example, the aluminum trialkyl should have a maximum aluminum hydride equivalent of not more than about 0.8 weight percent. In preferred embodiments the aluminum trialkyl as fed to the process is essentially hydride-free, that is, the trialkylaluminum product contains, if any, a maximum of 0.10 weight percent of aluminum hydride equivalent, and more preferably a maximum of 0.05 weight percent of aluminum hydride equivalent, because the aluminum hydride bond can cause isomerization of 1-olefins to internal olefins.

The preferred aluminum alkyls are the tri-$C_{1-12}$ alkyl aluminum such as trimethyl aluminum, triethyl aluminum, tributyl aluminum, tri-isobutyl aluminum, trioctyl aluminum, tridecyl aluminum, tridodecyl aluminum and the like including mixtures thereof. The more preferred aluminum alkyls are the higher aluminum alkyl such as the tri-$C_{4-10}$ alkyl aluminum. Most preferably the alkyls bonded to aluminum have the same or dose to the same number of carbon atoms as the vinyl olefin starting material. For example, tri-n-octyl aluminum is the most preferred catalyst for dimerizing 1-octene.

The reaction should be conducted in an environment that is essentially anhydrous and substantially free of oxygen and air. Aluminum trialkyls can react violently with water or compounds containing hydroxyl groups such as alcohols. Thus even a small amount of water, alcohol, or the like, in the system will inactivate some of the aluminum trialkyl. If it known that some water is present in the vinyl olefin, by use of analysis such as Karl Fischer water analysis, the amount of aluminum alkyl catalyst can be increased in order to compensate for the water or other active hydrogen component such as alcohol whereby the proper amount of active aluminum trialkyl catalyst remains in the system even after part of the initial aluminum alkyl has been destroyed by the water or other active hydrogen compound. Alternatively, the olefin feed can be pretreated to remove water or alcohol contamination. Likewise the process should be conducted under a dry inert atmosphere, for example, nitrogen, argon, neon, or the like, to prevent catalyst destruction.

The dimerization is performed at an initial mole ratio of aluminum alkyl to vinyl olefin in the range of from about 0.01:1, preferably from about 0.6:1, to about 1.5:1, preferably to about 1.0:1, at a temperature in the range of from about 200° C., to about 288° C., preferably to about 260° C., more preferably to about 232° C. and for the period of time in the range of from about 30 to about 120 minutes. Within these ranges the conditions are selected to convert initial vinyl olefins at a selectivity for the formation of the combination of vinylidenes and deep internal olefins of at least 50 mole percent, preferably at least 70 mole percent, more preferably at least 80 mole percent.

FIG. 1 contains plots from a computer simulation of the conversion of 1-octene to vinylidenes and deep internal olefins having 16 or 18 carbon atoms versus reaction temperature and at a reaction time of 30 minutes at each of 5 different initial mole ratios of aluminum alkyl to vinyl olefin. The plots illustrate that the maximum selectivities for the formation of the combination of $C_{16-18}$ vinylidenes and deep internal olefins are in the range of from about 80 to about 86 weight percent of initial vinyl olefin converted to the combination of $C_{16-18}$ vinylidenes and deep internal olefins, that this maximum conversion to the combination of $C_{16-18}$ vinylidenes and deep internal olefins takes place at a temperature in the range of 205° C. to 260° C., and that the temperature for this maximum conversion decreases within this range as the initial mole ratio of aluminum alkyl to vinyl olefin increases.

The dimerization product mixture comprises dimers (both vinylidenes and deep internal olefins), unreacted vinyl olefins, and internal monomeric olefins that are isomers of the initial vinyl olefins. Part or all of the mixture is introduced to the process for making vinyl olefins in the method of this invention. The high rate of the dimerization reaction and the high yield of the combination of $C_{16-18}$ vinylidenes and deep internal olefins under the conditions employed in the present invention permit the use of smaller vessels and shorter holdup times for the dimerization reaction and thereby permits the dimerization to be incorporated as a step into the process for manufacturing vinyl olefins.

The product mixture from the dimerization step comprises dimer products (both vinylidenes and deep internal olefins) unreacted vinyl olefins and deep internal olefins, of which all or part is incorporated into the feed to some step of the process for making vinyl olefins. In general, in the process for making vinyl olefins employed in the method of the present invention, ethylene is oligomerized on a trialkyl aluminum, typically triethylaluminum, in a continuous stoichiometric chain growth reactor at 120–150° C. and 14–21 MPa (140–210 atmospheres) for about an hour. Unreacted ethylene and other light olefins then separated by flashing and aluminum alkyl products are passed to a displacement step in which a low molecular weight alkene, typically ethylene or butylene, is used to displace the alkyl groups on the aluminum alkyl products, and the initial trialkyl aluminum, typically triethyl aluminum, is regenerated. This displacement step is performed at 280–320° C. and 1.0 MPa (10 atmospheres) with a minimum contact time. The alkyl groups on the aluminum alkyl products are displaced in this step primarily as vinyl olefins with small amounts of internal olefins that are monomeric isomers of the vinyl olefins.

The aforesaid vinyl olefins can be separated from trialkyl aluminum and recovered at various stages in the process. If not removed at this juncture, the vinyl olefins can be treated in a second chain growth step and thereby converted to longer chain alkyl groups in higher molecular weight aluminum alkyl products. After removal of unreacted ethylene and other light olefins, these higher molecular weight aluminum alkyl products can then be treated in second displacement step, as described above, whereby the longer chain alkyl groups are displaced as longer chain vinyl olefins. These longer chain vinyl olefins can be separated from trialkyl aluminum and recovered or can be treated in another chain growth step. Thus, vinyl olefins produced in this process can be removed and recovered before or after one or more additional chain growth steps.

In a more detailed embodiment (step a) triethyl aluminum and ethylene are fed to a first ethylene chain growth reaction zone maintained under ethylene chain growth conditions to form a first chain growth product. Unreacted ethylene is separated (step b) from the first chain growth product mixture to form an ethylene-depleted first chain growth product, which is then distilled (step c), whereby $C_{4-14}$ vinyl olefins are distilled from the ethylene-depleted first chain growth product leaving a bottoms fraction or stream comprising mainly poisson distributed tri-$C_{2-20+}$ alkyl aluminum and $C_{14+}$ vinyl olefins. At least part of the bottom fraction or stream is then conveyed (step d) to an ethylene or $C_{4-8}$ olefin displacement zone maintained under displacement conditions and feeding ethylene or $C_{4-8}$ olefins, to the displacement zone thereby forming an ethylene- or $C_{4-8}$ olefin-displaced product, respectively, comprising mainly triethyl or tri-$C_{4-8}$ alkyl aluminum, ethylene and $C_{4-20}$ vinyl olefins. The resulting ethylene- or $C_{4-8}$ olefin is placed product is next conveyed (step e) to a second ethylene chain growth reaction one maintained under chain growth conditions and feeding ethylene to the second thylene chain growth reaction zone to thereby form a second chain growth product comprising mainly ethylene, $C_{4-20}$ vinyl olefins and poisson distributed tri-$C_{4-20}$ alkyl aluminums. Ethylene is then (step f) vaporized from the second chain growth product forming an ethylene-depleted second chain growth product, which is then (step g) stilled to separate $C_{4-14}$ vinyl olefins as overhead and leaving a bottoms fraction or stream comprising mainly poisson distributed tri-$C_{2-20+}$ alkyl aluminum and $C_{14+}$ vinyl olefins.

Another preferred embodiment of the process for making vinyl olefins in the method of the present invention includes both a $C_{4-8}$ olefin displacement loop and an ethylene displacement loop. In this embodiment any $C_{4-8}$ olefin formed in either loop can be used as feed olefin to a $C_{4-8}$ olefin displacement reactor. This dual loop process includes steps (a) through (g) as stated above and also includes the additional steps (h), (i) and (j). In step (h) a portion of the bottoms stream from step (c) is charged to an ethylene displacement zone maintained under displacement conditions, and ethylene is fed to this displacement zone thereby forming an ethylene-displaced product comprising mainly triethyl aluminum, ethylene and $C_{4-20+}$ vinyl olefins. In step (i) $C_{2-12}$ vinyl olefins are distilled from the ethylene-displaced product forming a bottoms fraction or stream comprising mainly triethyl aluminum and $C_{14+}$ vinyl olefins. In step A) this bottoms fraction or stream is recycled to the first ethylene chain growth reaction zone as described above.

Figure 2:
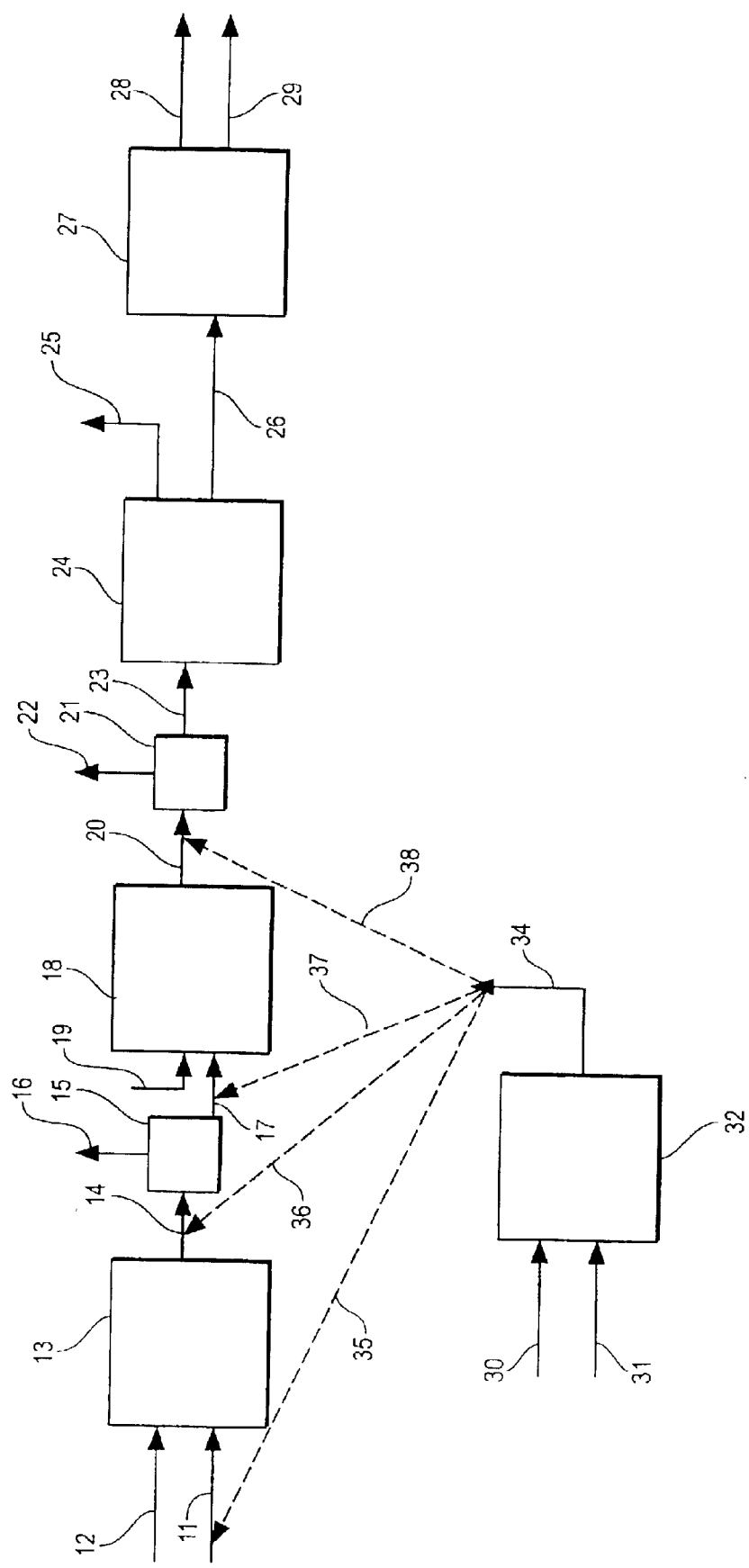
FIG. 2 is a schematic illustration of several preferred embodiments of the integration of the process for dimerizing vinyl olefins with a process for producing vinyl olefins and introducing into the process for producing vinyl olefins the entire dimerization product mixture.
Figure 3:
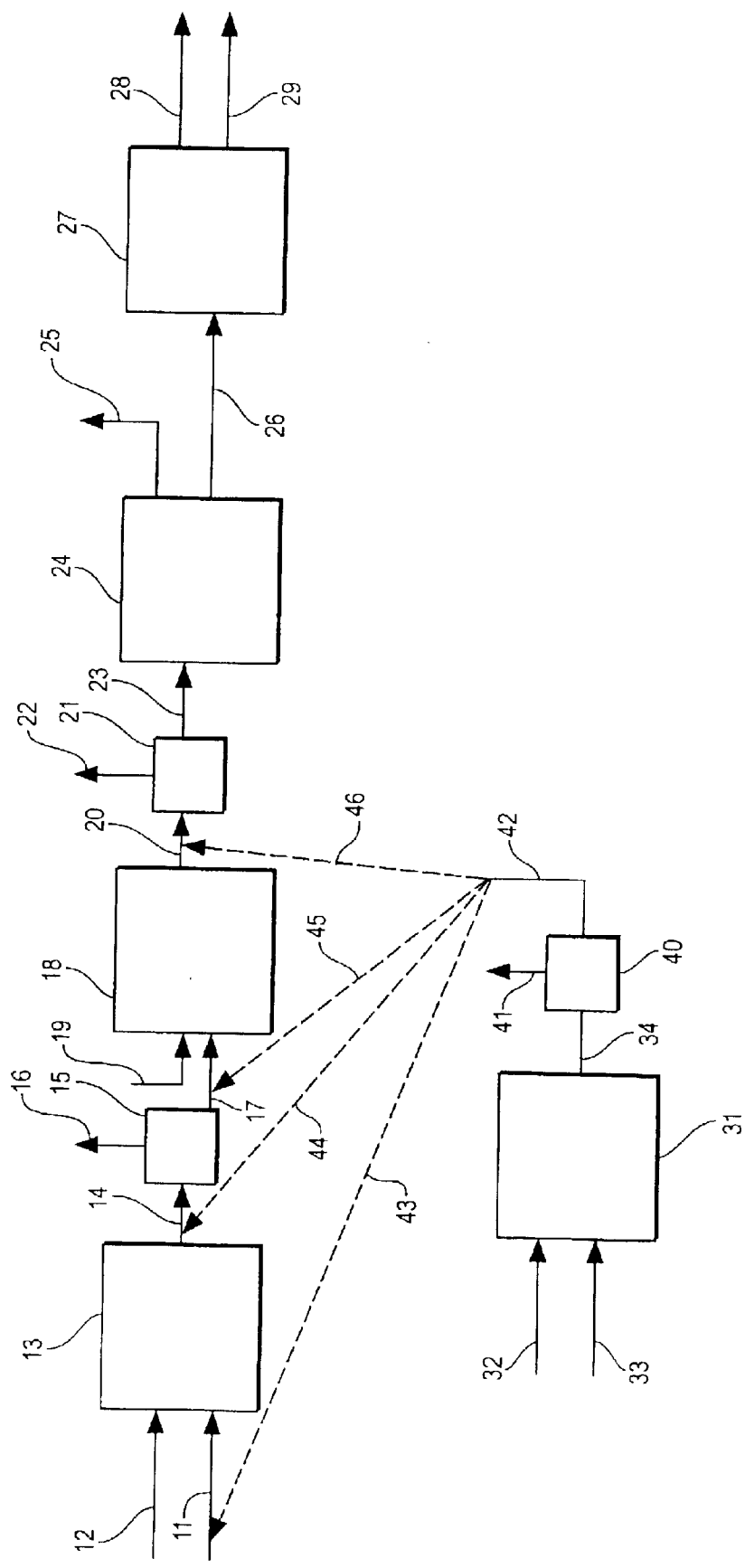
FIG. 3 is a schematic illustration of additional preferred embodiments of the integration of the process for dimerizing vinyl olefins with a process for producing vinyl olefins and introducing into the process for producing vinyl olefins a heavier fraction of the dimerization product mixture.

As illustrated in FIGS. 2 and 3, all or part of the dimerization product mixture can be introduced into any of several steps of the aforesaid process for making vinyl olefins. In FIG. 2, ethylene and chain growth catalyst are introduced through lines 11 and 12, respectively, into the chain growth reactor 13 from which the chain growth product mixture comprising chain growth product and unreacted ethylene is withdrawn through line 14. Unreacted ethylene is separated from the chain growth product mixture using a conventional separator 15 such as a distillation column and removed through line 16. The ethylene-depleted chain growth product mixture comprising mainly poisson distributed alkyl aluminum chain growth product is then passed through line 17 to a displacement reactor 18 which is maintained under displacement conditions. A low molecular weight olefin, typically ethylene or butylene, is introduced through line 19 into the displacement reactor 18 to thereby form in the displacement reactor 18 on ethylene- or butylene-displaced product comprising mainly vinyl olefins, triethyl or tributyl aluminum and ethylene or butylene. This displacement product mixture is withdrawn from the displacement reactor 18 through line 20. Ethylene, butylene and other light olefins are then removed from the displacement reactor mixture using a separator 21, typically a distillation column, and withdrawn through line 22. The remaining displacement product mixture is fed through line 23 to a gas liquid separator 24 wherein a gaseous fraction comprising trialkyl aluminums is separated and withdrawn through line 25. The liquid fraction comprising the desired vinyl olefin products in withdrawn through line 26 to a distillation column 27 where they are separated into lighter and heavier fractions. The lighter fraction comprising vinyl olefins is withdrawn through line 28 and a heavier fraction is withdrawn through line 29.

Vinyl olefin and dimerization catalyst are introduced through lines 30 and 31 into dimerization reactor 32 from which the dimerization product mixture comprising dimeric vinylidenes, dimeric deep internal olefins, monomeric internal olefins and monomeric unreacted vinyl olefins is withdrawn through line 34. In one series of alternatives, the dimerization product mixture is then fed in its entirety (a) through line 35 to and combined in line 11 with the feed to the chain growth reaction 13, (b) through line 36 to and combined in line 14 with the chain growth product (c) through line 37 to and combined in line 17 with the feed to the displacement reactor 18, or (d) through line 38 to and combined in line 20 with the displacement product mixture, These alternatives are indicated by broken lines 35, 36, 37 and 38.

FIG. 3 illustrates another series of alternatives in which the dimerization product mixture is conducted from the dimerization reactor 32 through line 34 and introduced into a vapor/liquid separator 40, from which the vapor fraction is withdrawn through line 41 and the liquid fraction which comprises olefin dimers and aluminum alkyls is withdrawn through line 42 and ($a^1$) conducted through line 43 to and combined in line 11 with the feed to the chain growth reactor 13, ($b^1$) conducted throught line 44 to and combined in line 14 with the chain growth product, ($c^1$) through line 45 to and combined in line 17 with the feed to the displacement reactor 18, or ($d^1$) through line 46 to and combined in line 20 with the displacement product mixture. These alternatives are indicated by broken lines 43, 44, 45 and 46. All processing elements in FIG. 3 which correspond to processing elements in FIG. 2 are identified by the same numerals and perform the same function, Thus, in the method of the present invention, either all or at least the liquid fraction of the dimerization product mixture is combined with either (1) the feed to or (2) product mixture from the chain growth reactor or (3) the feed to or (4) product mixture form the displacement reactor. In this way, the entire dimerization product mixture is recovered, and much of the recovered amount is utilized in the process for manufacturing vinyl olefins. For example, depending on where in the process for manufacturing vinyl olefins that at least a portion of the dimerization product is introduced, the chain length of at least some components of the dimerization product mixture can be altered in the chain growth or displacement step, and/or the combination of the dimerization product mixture with the particular stream in the vinyl olefin manufacturing process can afford the desired carbon number distribution. Such combination also permits the maximum dimerization operating temperatures and dimer production rates to be used because they are no loner limited by the amount of by-product olefins as a result of the unreacted vinyl olefins from the dimerization step. The dimers are withdrawn from the process through line 29.

The present invention will be more clearly illustrated, but not limited, by the following specific examples.

EXAMPLES 1–14

A glass pressure vessel was dried and purged with nitrogen and then charged with varying amounts of one or more vinyl olefins and of one or more trialkyl aluminums and heated at various temperatures in excess of 200° C. for varying periods of time. The amounts of vinyl olefins and trialkyl aluminum and the reaction temperatures and times in each example are indicated in Table 1. The weight percent of vinyl olefin converted and the selectivities for the formation of $C_{16}$ dimer (both vinylidenes and deep internal $C_{16}$ olefins combined), internal $C_8$ olefins, branched $C_8$ paraffins are also presented in Table 1. The selectivites are determined as the weight percent of the particular product produced per the weight percent of feed that is converted.

From the above description, it is apparent that the objects of the present invention have been achieved. While only certain embodiments have been set forth, alternating embodiments and various modifications will be apparent from the above description to those skilled in the art. These alternatives are considered equivalents and are within the spirit and scope of the present invention.

TABLE 1

| Example No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Vinyl olefin charge (g) | | | | | | | | | | | | | | |
| 1-octene | 30 | 35 | 35 | 35 | 35 | 35 | 35 | 35 | 35 | 35 | 35 | 35 | 27.5 | 27.5 |
| 1-decene | | | | | | | | | | | | | 9.5 | 9.5 |
| Trialkyl aluminum charge (g) | | | | | | | | | | | | | | |
| Tri-n-octyl aluminum | 4.25 | 1.67 | 3.33 | 5 | 5 | 1.67 | 5 | 1.67 | 1.67 | | | 1.67 | 5 | 5 |
| Tri-i-butyl aluminum | | | | | | | | | | 2.7 | 1.35 | | | |
| Initial Mole Ratio of Trialkyl aluminum to vinyl olefin | 0.04 | 0.01 | 0.03 | 0.04 | 0.04 | 0.01 | 0.04 | 0.01 | 0.01 | 0.04 | 0.02 | 0.01 | 0.04 | 0.04 |
| Temperature (° C.) | 206 | 206 | 206 | 223 | 223 | 234 | 262 | 262 | 262 | 262 | 262 | 262 | 206 | 206 |
| Reaction time (hr.) | 2 | 2 | 2 | 1 | 0.5 | 2 | 0.5 | 0.5 | 0.5 | 0.5 | 0.5 | 1 | 1 | 0.5 |
| Vinyl olefin conversion (wt. %) | 93 | 75 | 95 | 93 | 65 | 99 | 98 | 41 | 48 | 99 | 93 | 96 | 86 | 63 |
| Selectivity (wt. %) for the formation of | | | | | | | | | | | | | | |
| $C_{16}$ Dimers | 83 | 89 | 84 | 83 | 75 | 70 | 73 | 83 | 83 | 62 | 68 | 68 | 83 | 82 |
| Internal $C_8$ olefins | 15 | 9 | 11 | 15 | 23 | 19 | 17 | 12 | 15 | 20 | 19 | 22 | 11 | 12 |
| Branched $C_8$ olefins | 1 | 0 | 0 | 1 | 2 | 0 | 1 | 2 | 2 | 1 | 1 | 1 | — | — |

Having described the invention, what is claimed is:

1. In a process for manufacturing vinyl olefins containing from 4 to 30 carbon atoms, comprising:

(1) reacting ethylene in a chain growth reaction in the presence of an alkyl aluminum chain growth catalyst in at least one chain growth step;

(2) displacing the alkyl moieties of the resulting aluminum alkyl chain growth product in at least one displacement step to form a displacement product mixture comprising the corresponding vinyl olefins formed from the alkyl moieties;

(3) fractionating the displacement product mixture from at least one aforesaid displacement step to separate a liquid fraction comprising vinyl olefins containing from 4 to 30 carbon atoms; and (4) fractionating the resulting liquid fraction to separate therefrom a lower molecular weight fraction comprising vinyl olefins;

the improvement which comprises:

(5) dimerizing vinyl olefins to form vinylidenes and deep internal olefins in the presence of an alkyl aluminum dimerization catalyst comprising alkyl aluminum at an initial molar ratio of alkyl aluminum to vinyl olefins of from about 0.01 to about 1.5:1 and at a temperature in the range of from 200° C. to about 288° C. for a period of time in the range of from about 30 minutes to about 120 minutes to thereby convert vinyl olefins at a selectivity for the formation of vinylidenes and deep internal olefins combined of at least 50 mole percent; and (6) treating the resulting dimerization product mixture by
        (a) combining it in its entirety with the feed to at least one aforesaid chain growth step (1) or to at least one aforesaid displacement step (2); or
        (b) combining it in its entirety with the product mixture from the least one aforesaid chain growth step (1) or with the product mixture from at least one aforesaid displacement step (2); or
        (c) fractionating it to separate a light olefin fraction and a heavier fraction comprising vinylidenes and deep internal olefins which heavier fraction is then treated as in step (a) or (b);

such that the resulting displacement product mixture comprises vinylidenes and deep internal olefins from the dimerization product mixture or chain growth products of such vinylidenes and deep internal olefins which are separated with the aforesaid vinyl olefins in the liquid fraction separated in step (3) and are subsequently separated as the higher molecular weight fraction from the vinyl olefins in step (4).

2. The process of claim 1 wherein the initial molar ratio of the alkyl aluminum dimerization catalyst is to vinyl olefins is from about 0.6:1 to about 1.5:1.

3. The process of claim 2 wherein the initial molar ratio of alkyl aluminum dimerization catalyst to vinyl olefins is from about 0.6:1 to about 1.0:1.

4. The process of claim 1 wherein the dimerization is performed at a temperature in the range of from about 200° C. to about 260° C.

5. The process of claim 4 wherein the dimerization is performed at a temperature in the range of from about 200° C. to about 232° C.

6. The process of claim 1 wherein at least 80 weight percent of vinyl olefins are converted in the dimerization.

7. The process of claim 6 wherein at least 90 weight percent of vinyl olefins are converted in the dimerization.

8. The process of claim 1 wherein the selectivity for the formation of vinylidenes and deep internal olefins in the dimerization is at least 70 mole percent.

9. The process of claim 8 wherein the selectivity for the formation of vinylidenes and deep internal olefins in the dimerization is at least 80 mole percent.

10. The process of claim 1 wherein in step (6) the dimerization product mixture in its entirety is combined with the feed to at least one chain growth step (1) or to at least one displacement step (2).

11. The process of claim 1 wherein steps (6) the dimerization product mixture in its entirety is combined with the product mixture from at least one chain growth step (1) or with the product mixture from at least one displacement step (2).

12. The process of claim 1 wherein in step (6) the dimerization product mixture is fractionated in step (6)(c).

* * * * *

UNITED STATES PATENT AND TRADEMARK OFFICE
CERTIFICATE OF CORRECTION

PATENT NO. : 6,756,514 B1
DATED : June 29, 2004
INVENTOR(S) : George Barac et al.

It is certified that error appears in the above-identified patent and that said Letters Patent is hereby corrected as shown below:

Column 7,
Line 49, "In step (j) this bottom fraction or stream" should read
-- In step A) this bottom fraction or stream --

Signed and Sealed this

Thirtieth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,756,514 B1
DATED : June 29, 2004
INVENTOR(S) : Geroge Barac et al.

It is certified that error appears in the above-identified patent and that said Letters Patent is hereby corrected as shown below:

Column 5,
Line 47, reads "have the same or dose to the same number" should read
-- have the same or close to the same number --.

Column 7,
Line 49, reads, "In step A) this bottom fraction or stream" should read
-- In step (j) this bottom fraction or stream --.

Signed and Sealed this

Thirtieth Day of August, 2005

JON W. DUDAS
*Director of the United States Patent and Trademark Office*